(12) United States Patent
Stroffolino, IV et al.

(10) Patent No.: US 11,180,368 B2
(45) Date of Patent: Nov. 23, 2021

(54) METHOD FOR MIXING AT LEAST TWO GASES

(71) Applicant: L'Air Liquide, Société Anonyme pour l'Etude et l'Exploitation des Procédés Georges Claude, Paris (FR)

(72) Inventors: Joseph T. Stroffolino, IV, Pearland, TX (US); Alexander Roesch, Butzbach (DE)

(73) Assignee: L'Air Liquide, Société Anonyme pour l'Etude et l'Exploitation des Procëdës Georges Claude, Paris (FR)

( * ) Notice: Subject to any disclaimer, the term of this patent is extended or adjusted under 35 U.S.C. 154(b) by 51 days.

(21) Appl. No.: 16/707,589

(22) Filed: Dec. 9, 2019

(65) Prior Publication Data

US 2021/0171342 A1    Jun. 10, 2021

(51) Int. Cl.
*C01B 3/02* (2006.01)
*B01D 53/047* (2006.01)
*B01F 3/02* (2006.01)
*C01C 1/04* (2006.01)

(52) U.S. Cl.
CPC ............ *C01B 3/025* (2013.01); *B01D 53/047* (2013.01); *B01F 3/028* (2013.01); *C01C 1/04* (2013.01); *C01B 2203/0205* (2013.01); *C01B 2203/061* (2013.01); *C01B 2203/068* (2013.01); *C01B 2203/1671* (2013.01)

(58) Field of Classification Search
CPC ............ C01B 3/025; C01B 2203/0205; C01B 2203/1671; C01B 2203/061; C01B 2203/068; C01C 1/04; B01D 53/047
See application file for complete search history.

(56) References Cited

U.S. PATENT DOCUMENTS

| | | | |
|---|---|---|---|
| 2015/0141535 A1* | 5/2015 | Kresnyak | C10G 45/02 518/702 |
| 2016/0083260 A1* | 3/2016 | Dahl | C01B 3/48 423/359 |

* cited by examiner

*Primary Examiner* — Jafar F Parsa
(74) *Attorney, Agent, or Firm* — Elwood L. Haynes

(57) ABSTRACT

A method of co-producing a nitrogen containing stream and a methanol stream, including producing at least an oxygen enriched stream and a nitrogen enriched stream in an air separation unit, introducing at least a portion of the oxygen enriched stream into an oxygen-based reformer, thereby producing a first syngas stream, introducing at least a portion of the first syngas stream into a methanol synthesis reactor, thereby producing at least a hydrogen containing stream and a methanol containing stream, introducing at least a portion of the methanol containing stream into a methanol distillation system, thereby producing a methanol product stream, introducing at least a portion of the nitrogen enriched stream, at least a portion of the first enriched hydrogen containing stream, and at least a portion of the second enriched hydrogen containing stream into an ammonia synthesis reactor, thereby producing an ammonia product stream.

19 Claims, 3 Drawing Sheets

METHOD FOR MIXING AT LEAST TWO GASES

BACKGROUND

It is a widespread practice to develop and construct separate processes for the industrial production of methanol and either ammonia or urea and to manufacture each of these products at a time. From an economic viewpoint it is however advantageous to manufacture methanol as well as either ammonia or urea in a single process sequence, because by that the costs in comparison to separate process sequences for each product are decreased considerably. The costs will be lowered not only for carrying out the manufacturing method, but also already by smaller purchases of equipment sites required for manufacturing the plant.

SUMMARY

A method of co-producing a nitrogen-containing stream and a methanol stream, including producing at least an oxygen enriched stream and a nitrogen enriched stream in an air separation unit, introducing at least a portion of the oxygen enriched stream into an oxygen-based reformer, thereby producing a first syngas stream, introducing at least a portion of the first syngas stream into a methanol synthesis reactor, thereby producing at least a hydrogen-containing stream and a methanol-containing stream, introducing at least a portion of the methanol-containing stream into a methanol distillation system, thereby producing a methanol product stream, introducing at least a portion of the hydrogen-containing stream into a first hydrogen separator, thereby producing a first enriched hydrogen-containing stream, producing a second syngas stream in a steam methane reformer, introducing at least a portion of the second syngas stream into a second hydrogen separator, thereby producing a second enriched hydrogen-containing stream, and introducing at least a portion of the nitrogen enriched stream, at least a portion of the first enriched hydrogen-containing stream, and at least a portion of the second enriched hydrogen-containing stream into an ammonia synthesis reactor, thereby producing an ammonia product stream.

BRIEF DESCRIPTION OF THE FIGURES

For a further understanding of the nature and objects for the present invention, reference should be made to the following detailed description, taken in conjunction with the accompanying drawings, in which like elements are given the same or analogous reference numbers and wherein.

ELEMENT NUMBERS

Figure 1:
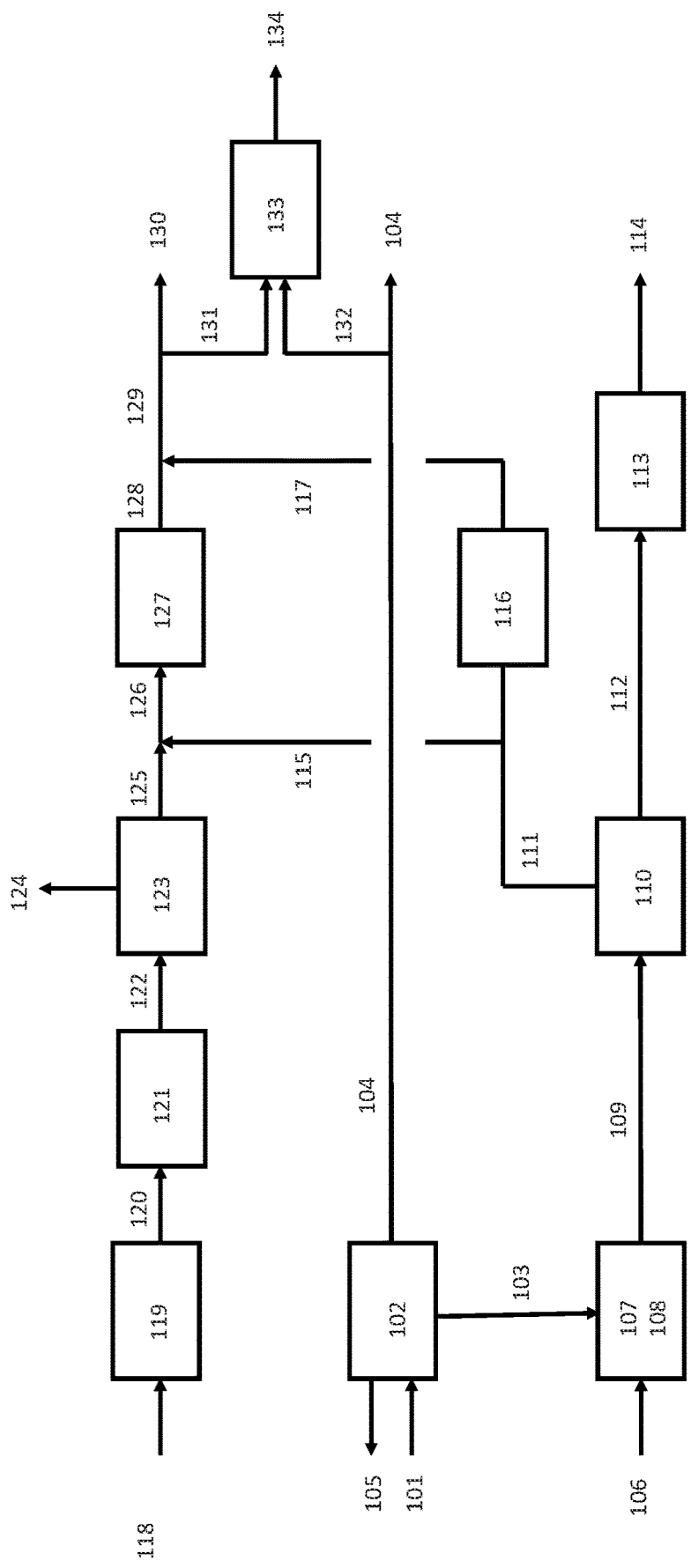
FIG. 1 is a schematic representation in accordance with one embodiment of the present invention.

101=inlet air (to ASU)
102=ASU
103=oxygen rich stream (from ASU)
104=nitrogen rich stream (from ASU)
105=argon rich stream (from ASU)
106=first natural gas stream (to combined reforming)
107=ATR (combined reforming)
108=(first) SMR (combined reforming)
109=first syngas stream
110=methanol synthesis reactor
111=first hydrogen-containing stream (from methanol synthesis reactor)
112=methanol-containing stream (from methanol synthesis reactor)
113=methanol distillation system
114=methanol product stream
115=third hydrogen-containing stream (to carbon dioxide poor syngas stream)
116=first PSA
117=first enriched hydrogen stream (from first PSA)
118=second natural gas stream (to combined reforming)
119=second SMR
120=second syngas stream
121=water-gas shift reactor (HT, LT, or both)
122=shifted second syngas stream
123=carbon dioxide separator
124=carbon dioxide enriched stream (from carbon dioxide separator)
125=carbon dioxide poor syngas stream (from carbon dioxide separator)
126=hydrogen enhanced stream
127=second PSA
128=second enriched hydrogen stream (from second PSA)
129=combined enriched hydrogen stream
130=hydrogen product stream
131=hydrogen rich stream (to ammonia synthesis)
132=nitrogen rich stream (to ammonia synthesis)
133=ammonia production
134=ammonia product stream
135=carbon dioxide enriched stream to urea synthesis
136=urea production
137=urea product stream
138=urea synthesis
139=carbon dioxide product stream
140=ammonia stream to urea synthesis

DETAILED DESCRIPTION OF PREFERRED EMBODIMENTS

Illustrative embodiments of the invention are described below. While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

It will of course be appreciated that in the development of any such actual embodiment, numerous implementation-specific decisions must be made to achieve the developers specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

A method for leveraging nitrogen from a new or existing Air Separation Unit (ASU), which provides oxygen to produce methanol syngas, to supply an ammonia synthesis loop is provided. The hydrogen sourced from methanol synthesis loop purge gas is also leveraged, which offsets the on-purpose hydrogen production investment, to supply an ammonia synthesis loop. An on-purpose hydrogen production may be installed, if necessary, to meet the balance of the demand required for the ammonia synthesis loop.

The ammonia loop is supplied pure nitrogen and pure hydrogen eliminating all or most of the need for a purge or purge recovery and reducing operational expense of the loop. $CO_2$ may be recovered from the on-purpose hydrogen production unit, if one is utilized, for use to produce urea, either from process gas or flue gas, or both. A shared utility park may be utilized to further reduce investment, which may be an "over the fence" model for utilities such as water. The methanol purge gas may be sent directly to an on-purpose second PSA.

Figure 2:
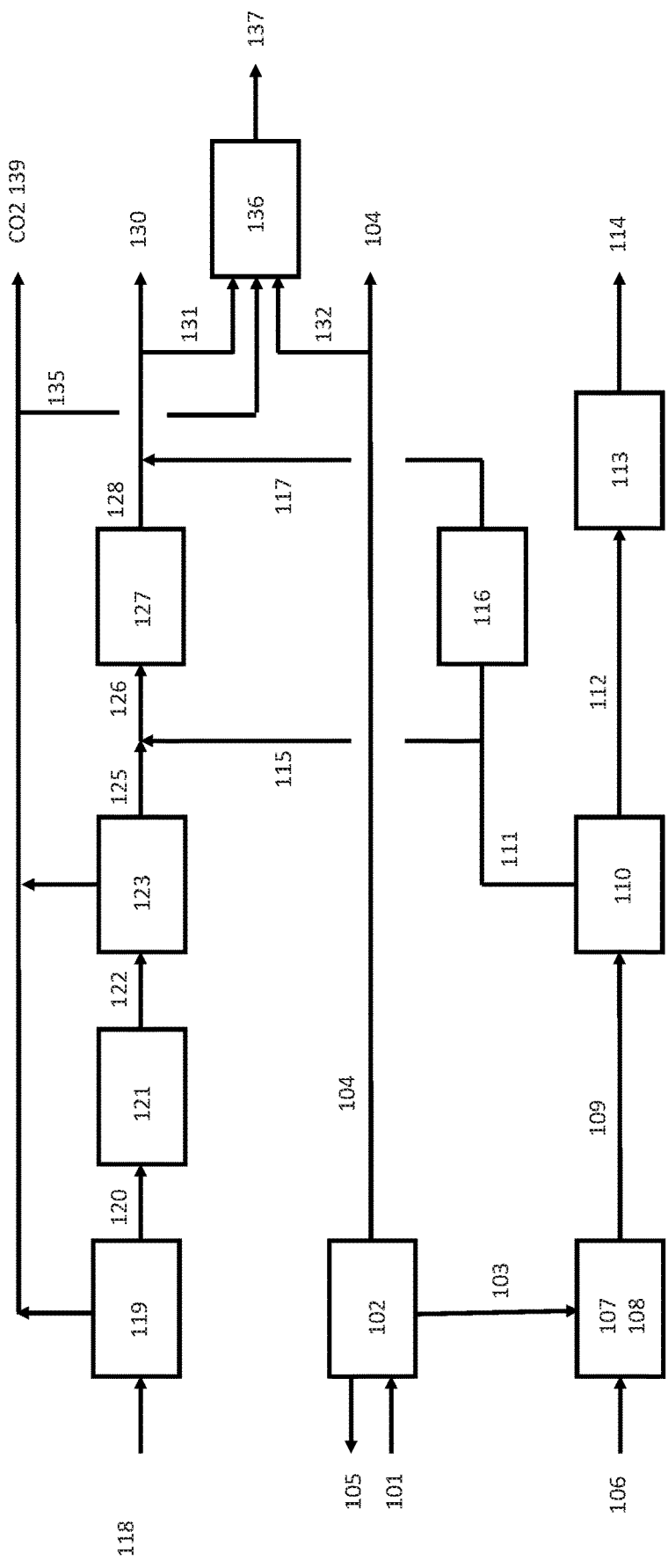
FIG. 2 is a schematic representation in accordance with one embodiment of the present invention.
Figure 3:
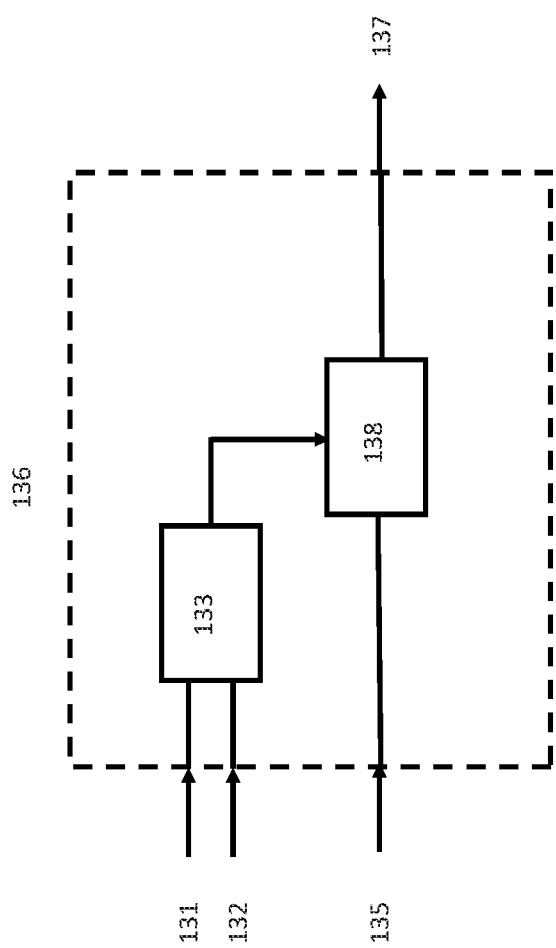
FIG. 3 is a schematic representation in accordance with one embodiment of the present invention.

The present invention may be better understood with reference to FIGS. 1-3.

In one embodiment of the present invention, a method of co-producing a nitrogen-containing stream and a methanol stream is provided, Inlet air stream 101 is introduced into ASU 102, thereby producing at least oxygen rich stream 103 and nitrogen rich stream 104. Argon rich stream 105 may also be produced and exported.

At least a portion of oxygen rich stream 103 is introduced, along with first hydrocarbon fuel stream 106, into an oxygen-based reformer 107, thereby producing first syngas stream 109. First hydrocarbon fuel stream 106 may be natural gas. Oxygen-based reformer 107 may be an autothermal reformer (ATR). Oxygen based reformer 107 may be an ATR combined with a stream methane reformer (SMR) 108, in what is known in the art as a combined reformer. Oxygen based reformer 107 may be in parallel with SMR 108. Oxygen based reformer 107 may be in series with SMR 108.

At least a portion of first syngas stream 109 is introduced into methanol synthesis reactor 110, thereby producing at least first hydrogen-containing stream 111 and methanol-containing stream 112. At least a portion of methanol-containing stream 112 is introduced into methanol distillation system 113, thereby producing methanol product stream, 114. At least a portion of first hydrogen-containing stream 111 is introduced into first hydrogen separator 116, thereby producing first enriched hydrogen-containing stream 117. First hydrogen separator may be a pressure swing adsorber (PSA). Methanol synthesis reactor 110, methanol distillation system 112, and or air separation unit 102 may be part of a pre-existing facility.

Second hydrocarbon stream 118 is introduced into second SMR 119, thereby producing second syngas stream 120. At least a portion of second syngas stream 120 may be introduced into water-gas shift reactor 121, thereby producing shifted syngas stream 122. Water-gas shift reactor may be low temperature shift, a high temperature shift, or both. At least a portion of second syngas stream 120 is introduced into second hydrogen separator 127, thereby producing second enriched hydrogen-containing stream 128.

At least a portion first enriched hydrogen-containing stream 117 and second enriched hydrogen-containing stream 128 are combined to form combined enriched hydrogen stream 129. A portion 130 of combined enriched hydrogen stream 129 may be exported as a product. At least a portion 132' of nitrogen enriched stream 104, at least a portion 131 of combined enriched hydrogen stream are introduced into ammonia synthesis reactor 133, thereby producing ammonia product stream 134. Second hydrogen separator may be a pressure swing adsorber (PSA).

Carbon dioxide separator 123 may be located between second SMR 119 and second hydrogen separator 127, thereby producing carbon dioxide rich stream 124 and carbon dioxide poor syngas stream 125. Carbon dioxide separator 123 may be between water-gas shift reactor 121 and second hydrogen separator 127. At least a portion 135 of carbon dioxide rich stream 124 may be introduced, along with at least a portion of ammonia product stream 140, into urea synthesis reactor 138, thereby producing urea product stream 137. Ammonia reactor 133 and urea reactor 138 may be part of urea production system 136.

A portion 115 of first hydrogen-containing stream 111 may be combined with carbon dioxide poor syngas stream 125 thereby forming hydrogen enhanced stream 126. Hydrogen enhanced stream 126 may be introduced into second hydrogen separator 127.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method of co-producing a nitrogen-containing stream and a methanol stream comprising:
producing at least an oxygen enriched stream and a nitrogen enriched stream in an air separation unit,
introducing at least a portion of the oxygen enriched stream into an oxygen-based reformer, thereby producing a first syngas stream,
introducing at least a portion of the first syngas stream into a methanol synthesis reactor, thereby producing at least a hydrogen containing stream and a methanol containing stream,
introducing at least a portion of the methanol containing stream into a methanol distillation system, thereby producing a methanol product stream,
introducing at least a portion of the hydrogen containing stream into a first hydrogen separator, thereby producing a first enriched hydrogen containing stream,
producing a second syngas stream in a steam methane reformer,
introducing at least a portion of the second syngas stream into a second hydrogen separator, thereby producing a second enriched hydrogen containing stream,
introducing at least a portion of the nitrogen-enriched stream, at least a portion of the first enriched hydrogen-containing stream, and at least a portion of the second enriched hydrogen-containing stream into an ammonia synthesis reactor, thereby producing an ammonia product stream.

2. The method of claim 1, wherein the first hydrogen separator is a pressure swing adsorption unit.

3. The method of claim 1, wherein the second hydrogen separator is a pressure swing adsorption unit.

4. The method of claim 1, further comprising a water gas shift reactor downstream of the steam methane reformer and upstream of the second hydrogen separator.

5. The method of claim 1, wherein the oxygen-based reformer is an autothermal reformer.

6. The method of claim 5, further comprising a second steam methane reformer in parallel with the autothermal reformer.

7. The method of claim 5, further comprising a second steam methane reformer in series with the autothermal reformer.

8. The method of claim 1, wherein the air separation unit also produces an argon enriched stream.

9. The method of claim 1, wherein the autothermal reformer, the methanol synthesis reactor, and the methanol distillation system comprise a pre-existing facility.

10. The method of claim 1, wherein the air separation unit comprises a pre-existing facility.

11. The method of claim 1, further comprising a carbon dioxide separator downstream of the steam methane reformer and upstream of the hydrogen separator, thereby producing a carbon dioxide enriched stream at least a portion of which is introduced, along with at least a portion of the ammonia product stream, into a urea synthesis reactor, thereby producing a urea product stream.

12. The method of claim 11, wherein the first hydrogen separator is a pressure swing adsorption unit.

13. The method of claim 11, wherein the second hydrogen separator is a pressure swing adsorption unit.

14. The method of claim 11, further comprising a water gas shift reactor downstream of the steam methane reformer and upstream of the carbon dioxide separator.

15. The method of claim 11, further comprising a second steam methane reformer in parallel with the autothermal reformer.

16. The method of claim 11, further comprising a second steam methane reformer in series with the autothermal reformer.

17. The method of claim 11, wherein the air separation unit also produces an argon enriched stream.

18. The method of claim 11, wherein the autothermal reformer, the methanol synthesis reactor, and the methanol distillation system comprise a pre-existing facility.

19. The method of claim 11, wherein the air separation unit comprises a pre-existing facility.

* * * * *